(12) United States Patent
Chen et al.

(10) Patent No.: US 6,183,734 B1
(45) Date of Patent: Feb. 6, 2001

(54) INHIBITION OF TUMOR CELL GROWTH BY ADMINISTRATION OF B7-TRANSFECTED CELLS

(75) Inventors: Lieping Chen; Ingegerd Hellström; Karl Erik Hellström; Jeffrey A. Ledbetter; Peter S. Linsley, all of Seattle, WA (US)

(73) Assignee: Bristol-Myers Squibb Company, New York, NY (US)

( * ) Notice: Under 35 U.S.C. 154(b), the term of this patent shall be extended for 0 days.

(21) Appl. No.: 08/402,405

(22) Filed: Mar. 10, 1995

Related U.S. Application Data

(63) Continuation of application No. 08/161,183, filed on Dec. 1, 1993, now abandoned, which is a continuation of application No. 08/006,102, filed on Jan. 15, 1993, now abandoned, which is a continuation-in-part of application No. 07/956,123, filed on Oct. 2, 1992, now abandoned.

(51) Int. Cl.[7] .............................. A01N 63/00; A61K 48/00
(52) U.S. Cl. ................. 424/93.21; 424/93.7; 424/277.1; 424/278.1; 435/325; 435/240.2
(58) Field of Search .............................. 424/277.1, 93.21, 424/93.7, 278.1; 435/240.2, 325

(56) References Cited

FOREIGN PATENT DOCUMENTS

WO 92/00092   1/1992   (WO) .

OTHER PUBLICATIONS

Chen et al. (1992), Cell 71:1093–1102.
Jenkins et al. (1991), Journal of Immunology 147:2461–2466.
Chen et al. (1992), Journal of Immunology 148:2617–2621.
Linsley et al. (1990), Proc. Natl. Acad. Sci. USA 87:5031–5035.
Freeman et al. (1988), Journal of Immunology 143:2714–2722.
Jenkins et al. (1991), Journal of Immunology 147:2461–2466.
Harding et al. (1991), Nature 356:607–609.
Ley et al. (1991), Eur. J. Immunol. 21:851–854.
Gansbacher et al. (1990), J. Exp. Med. 172:1217–1224.
Fearon et al. (1990), Cell 60:397–403.
Linsley et al. (1991), J. Exp. Med. 173:721–730.
Restifo et al. (1991), Journal of Immunology, 147:1453–1459.
Restifo et al. (1992), J. Exp. Med. 177:265–272.
Azuma et al. (1992), Journal of Immunology, 149:1115–1123.
Chen et al. (1991), Proc. Natl. Acad. Sci.88:110–114.
Rosenberg et al. (1986), Science 233:1318–1321.
Liu et al. (1992), Eur. J. Immunol. 22:2855–2859.
Azuma et al. (1992), J. Exp. Med. 175:353–360.
Gimmi et al. (1991), Proc. Natl. Acad. Sci. USA 88:6575–6579.
Osband, M.E. et al. 1990. Immunol. Today 11:193–195.*
Fujiwara et al., Current Opinion in Oncology, vo. 6:96–105, Gene therapeutics and gene therapy for cancer, 1994.*
Culver et al., TIG, vol. 10(5):174–178, Gene therapy for cancer, 1994.*

* cited by examiner

*Primary Examiner*—Geetha P. Bansal
(74) *Attorney, Agent, or Firm*—Christopher A. Klein

(57) ABSTRACT

The present invention is directed to a method of inhibiting tumor cell growth. Tumor cells from a pateint are recombinantly engineered to express the B7 surface protein and these cells are then readminsistered to the pateint. The presence of the B7 molecule on the tumor cell surface stimulates a broad immunologic response against both the B7-transfected and non-transfected tumor cells and results in the immunologic killing of localized and metastatic tumor cells. B7 transfection of the tumor cells, or cell membranes, serves as a stimulant to engender a potent immunologic response against the surface antigens present on the tumor cells.

9 Claims, 8 Drawing Sheets

A

B

INHIBITION OF TUMOR CELL GROWTH BY ADMINISTRATION OF B7-TRANSFECTED CELLS

This is a file wrapper continuation of application Ser. No. 08/161,183, filed Dec. 1, 1993, now abandoned, which is a file wrapper continuation of application Ser. No. 08/006,102, filed Jan. 15, 1993, now abandoned, which is a continuation-in-part of application Ser. No. 07/956,123, filed Oct. 2, 1992, now abandoned.

BACKGROUND OF THE INVENTION

A longstanding goal of cancer research has been to stimulate the immunological rejection of tumors. This goal is based on the hypothesis that tumors express foreign antigens which can potentially serve as targets for the immune system (Himmelweit (1957) *The Collected Papers of Paul Ehrlich*, Pergamon Press, Oxford, England). Although it remains controversial to what extent spontaneous tumors express antigens which can be recognized as foreign by the immune system in conventional immunization and challenge experiments (Hewitt et al. (1976) Br. J. Cancer 33:241–259), it is well documented that many experimental tumors express antigens which can mediate tumor rejection in such experiments (Hellström and Hellström (1991) Principles of Tumor Immunity: Tumor Antigens, *In: The Biologic Therapy of Cancer*. DeVita, Jr. et al., Eds., J. B. Lippincott Co., Philadelphia, pp. 35–52; Boon (1992) Adv. Cancer Res. 58:177–211).

Cellular immunity, primarily mediated by T lymphocytes, plays the key role in the rejection of antigenic tumors. Both T helper cells (Th) and cytolytic T lymphocytes (CTL) are involved (Melief (1992) Adv. Cancer Res. 58:143–175; Greenberg (1991) Adv. Immunol. 49:281–355). Recognition and destruction of immunological targets require T lymphocyte recognition via the T cell receptor (TCR) of antigenic peptides presented in the context of MHC molecules (Bjorkman et al. (1988) Nature 329:512–518; Unanue (1984) Annu. Rev. Immunol. 2:395; Townsend et al. (1986) Cell 44:959–968). Although T cell immunity has been detected against specific tumor antigens in some animals and humans (van der Bruggen et al. (1991) Science 254:1643–1647; van den Eynde et al. (1991) J. Exp. Med. 173:1373–1384; Anichini et al., (1987) Immunol. Today 8:385–389), these "imunogenic" tumors generally grow progressively and eventually kill their hosts.

There are several reasons why even those tumors which express rejection antigens can evade immune destruction. They include the failure of tumors to adequately process and present antigens to T cells because of reduced levels of MHC class I expression (Elliot et al. (1989) Adv. Cancer Res. 53:181–244). A problem which might be circumvented by transfection with MHC class I genes (Hui et al. (1984) Nature 311:750–752; Tanaka et al. (1984) Science 228:26–30; Wallich et al. (1985) Nature 315:301–305) or with γ-interferon DNA which enhances antigen processing (Restifo et al. (1992) J. Exp. Med. 175:1423–1431). Lack of an effective antitumor immune response may also result from a deficiency in tumor-bearing animals of T helper functions necessary both for the clonal expansion of tumor-specific CTL (Fearon et al. (1990) Cell 60:397–403) and for the activation of macrophages and other inflammatory cells that can cause tumor destruction. Transfection of tumor cells with IL-2 or IL-4 cDNAs result in paracrine IL-2 secretion of lymphokines which substituted for T cell help, induced tumor-specific CTL, and cause tumor rejection (Fearon et al., (1990) Cell 60:397–403; Gansbacher et al. (1990) J. Exp. Med. 172:1217–1224; Ley et al. (1991) Eur. J. Immunol. 21:851–854; Golumbek et al. (1991) Science 254:713–716). Similarly, transfection of tumors with IL-4 cDNA can also cause tumor rejection (Tepper et al. (1989) Cell 57:503–512) and the generation of T cell-mediated tumor immunity (Golumbek et al. (1991) Science 254:713–716).

Another mechanism which may contribute to the induction of efficient tumor-reactive T cells is implicated from the two-signal models for immune cell activation. This model was originally proposed for B lymphocytes (Bretscher and Cohn (1970) Science 169:1042–1049) as an explanation for why antigens expressed on cells of nonhematopoetic origin are ineffective in inducing transplant rejection (Lafferty et al. (1983) Ann. Rev. Immunol. 1:143). Two-signal models have now been extended to all lymphocytes (Janeway (1989) Cold Spring Harbor Symp. Quant. Biol. 54:1–13; Nossal (1989) Science 245:147–153; Schwartz (1989) Cell 57:1073–1081). These models postulate that lymphocytes require for optimal activation both an antigen specific signal delivered through the antigen receptor, and a second, antigen non-specific or costimulatory signal. T cell costimulatory pathways determine whether TCR complex engagement results in immune cell activation or inactivation (Mueller et al. (1989) Annu. Rev. Immunol 7:445; Schwartz (1989) Cell 57:1073–1081) and antigen presentation in the absence of T cell costimulation leads to functional inactivation or clonal anergy or even cell death (Schwartz, (1989) Cell 57:1073–1081).

The molecular basis of T cell costimulation is not well understood, but may involve several molecules on antigen presenting cells (APC) which are recognized by T cell surface receptors (van Seventer et al. (1991) Curr. Opinion Immunol. 3:294–303). One important costimulatory molecule is B7 which is expressed on activated B cells (Freeman et al. (1989) J. Immunol. 143:2714) and other APC (Freeman et al., 1989; Razi-Wolf et al. (1992) Proc. Natl. Acad. Sci. USA 89:4210–4214). B7 binds to the CD28 (Linsley et al. (1990) Proc. Natl. Acad. Sci. USA 87:5031–5035) and CTLA-4 (Linsley et al. (1991) J. Exp. Med. 173:721–730) receptors on T cells and costimulates proliferation of human and murine CD4+ T cells (Linsley et al. (1991) J. Exp. Med. 174:561–569; Gimmi et al. (1991) Proc. Natl. Acad. Sci. USA 88:6575–6579; Kuolova et al. (1991) J. Exp. Med. 173:759–762; Damle et al. (1992) J. Immunol. 132:1985–1992). Experiments in vitro suggest that signals transduced by the CD28 receptor (June et al. (1990) Immunol. Today 11:211–216) can determine whether TCR occupancy results in a productive immune response or clonal anergy (Jenkins et al. (1991) J. Immunol. 147:2641–2466; Harding et al. (1992) Nature 356:607–609). Experiments in vivo indicate that blocking costimulation by B7 can effectively suppress humoral responses (Linsley et al. (1992) Science 257:792–795) and make possible long-term acceptance of tissue xenografts (Lenschow et al. (1992) Science 257:792–795).

The B7 molecule is expressed primarily on hematopoetic cells (Freeman et al. (1989) J. Immunol. 143:2714) and it is present only at very low levels, if at all, on many cultured human tumor cell lines. These findings suggest that one of the reasons why immunogenic tumors can often escape T cell destruction is that they lack appropriate costimulatory molecules. A prediction from this hypothesis is that introduction of costimulatory molecules into tumors which possess tumor rejection antigens would enhance their ability to induce specific anti-tumor immunity leading to tumor eradication in immunocompetent hosts. This hypothesis was tested using a murine model for tumors which express "rejection" antigens but which nonetheless grow progressively in their hosts. In this model, the human papillomavirus 16 (HPV-16) E7 gene was transfected into the poorly immunogenic K1735-M2 melanoma (Fidler and Hart (1981) Cancer Res. 41:3266–3267). A tumorigenic transfectant, E7C3, was selected, against which a CD8+ cell-mediated and HPV-16 E7-specific tumor immunity can be generated, by immunization of synegeneic C3H/HeN mice with E7-expressing fibroblasts (Chen et al. (1991) Proc. Natl. Acad. Sci. USA 88:110–114; Chen et al. (1992) J. Immunol. 148:2617–2621). The present invention demonstrates that transfection of E7C3 tumor cells with the costimulatory molecule B7 induces antitumor immunity to E7+ tumors.

SUMMARY OF THE INVENTION

The present invention is directed to a novel composition and method of effectively inhibiting tumor cell growth. In this method cells are removed from a tumor and then transfected with DNA encoding an immunogenic portion of the B7 ligand of B cells. The transfected tumor cells express B7 on their surface, and are then reinjected into the patient. The B7 transfected tumor cells effectively elicit an immune response which is directed against both the transfected and non-transfected tumor cells. Thus, the method of the present invention stimulates an immune response against the original tumor cells and metastases. The presence of B7 on the transfected cells serves as an unexpected catalyst or stimulant of this enhanced response. This method presents is the possibility of treating disseminated metastatic cancer by removing some cells from foci, transfecting or transducing these cells to express B7 and then readministering the transfected cells to a patient in order to stimulate a broad and specific immune response against the disseminated tumor cells. A pharmaceutical composition containing either recombinant tumor cells that have been transfected to express B7 or membranes of these cells expressing B7 is also contemplated in this invention The present invention also encompasses a method of immunizing a patient against specific tumor cells by administering B7-transfected tumor cell membranes to the patient in order to produce an immune response capable of inducing a rejection response or cell killing upon subsequent tumor cell exposure.

(A) Generation of CTL which lyse targets expressing the E7 gene in MHC class I restricted fashion. BC16 cells (5×10⁶) were injected subcutaneously into C3H/HeN mice. Spleens were removed from tumor-free mice and splenocytes were co-cultured with γ-irradiated 16N7 cells, and CTL activity towards $^{51}$Cr-labeled target cells was measured as described in Experimental Procedures. This and other cytotoxicity experiments were performed 3–5 times with similar results.

(B) Cytotoxic activity is mediated by CD8+ T cells. Effector cells generated from mice inoculated with BC22 cells were pretreated at 37° C. for 1 hr with anti-CD4, anti-CD8 or anti-asialoGM1 Abs in the presence of complement and washed twice before incubation with $^{51}$Cr-labeled 16N7 cells at different E:T ratios.

(C) CTL activity in mice injected with different tumors. C3H/HeN mice were injected subcutaneously with K1735-M2, E7C3, BC16 or irradiated (10,000 rad) E7C3 cells. After 4 weeks, splenocytes were prepared from the mice and cocultivated in vitro with γ-irradiated 16N7 cells for 6 days. Cytotoxic activity towards $^{51}$Cr-labeled 16N7 cells was then measured as described in Experimental Procedures.

Figure 2:
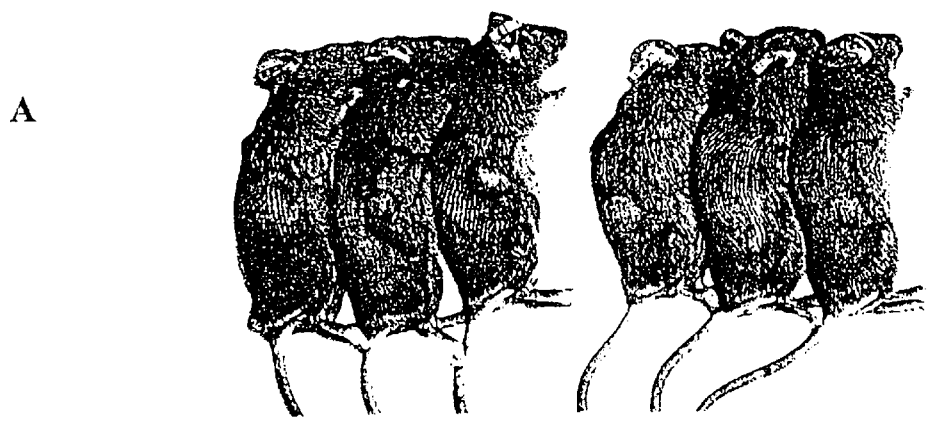
FIGS. 2A and 2B illustrate the tumors induced by B7+ E7C3 cells are rejected by immunocompetent, syngeneic C3H/HeN mice. (A) Photograph of tumors induced by B7− and B7+ E7C3 cells . C3H/HeN mice were injected subcutaneously with 5×10⁶ E7C3 cells (three mice on the left) or PB7+ cells (three mice on the right). The photograph was taken 21 days after tumor cell injection. (B) Kinetics of growth of tumors induced by B7− and B7+ E7C3 cells. C3H/HeN mice were injected subcutaneously with the indicated cells (5×10⁶). Tumors sizes were assessed weekly by measuring perpendicular diameters with a caliper. The results are expressed as mean diameters in millimeters of tumors from groups of five mice each. Error bars represent the standard deviation of the mean. Similar results were obtained in at least three experiments with each cell line.
Figure 2:
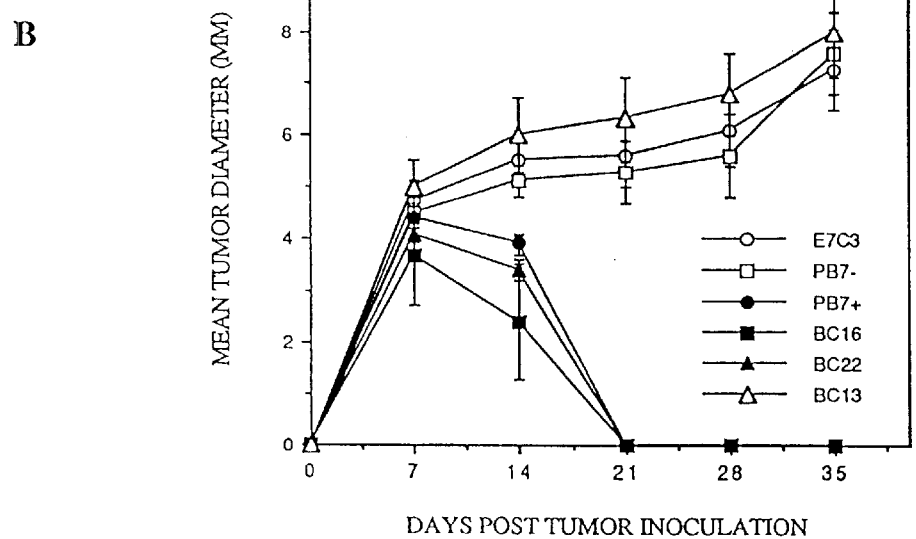
Figure 7:
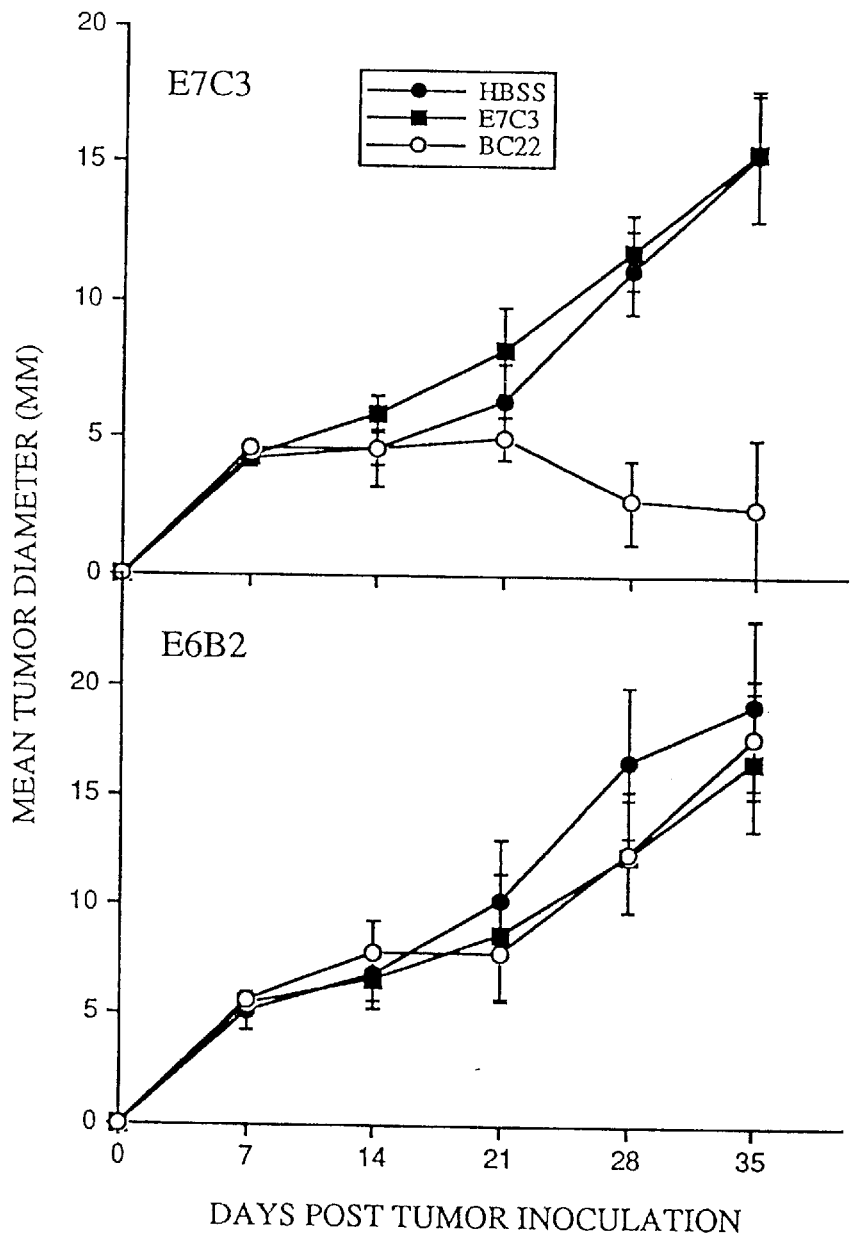

FIG. 7 illustrates that B7+ E7C3 cells induce immunity to B7− E7C3 tumors at a distant site. C3H/HeN mice were injected subcutaneously in their left flanks with HBSS, E7C3 or BC22 cells (5×10⁶). Immediately thereafter, mice were challenged by subcutaneous injection on the right flank with E7C3 (upper panel) or E6B2 (lower panel) cells (5×10⁶ cells). Growth of tumors in the right flank was measured as described in FIG. 2. Four of five animals injected with BC22 cells completely rejected E7C3 tumors, whereas progressive E7C3 tumor growth was seen with all other groups. This experiment was repeated again with similar results.

FIGS. 8A, 8B and 8C illustrate that B7⁺ E7C3 cells induce immunity against established metastatic tumors. C3H/HeN mice (10 per group) were injected intravenously with 1×10⁵ E7C3 (A), E6B2 (B) or K1735-M2 cells (C). Four days later, mice were treated by intravenous injection with BC16 cells (1×10⁶). Treatment was subsequently repeated twice more at five day intervals. Survival of tumor-bearing animals was monitored. Survival of animals without E7C3 tumors was unaffected by treatment with BC16 cells.

DESCRIPTION OF PREFERRED EMBODIMENTS

The present invention is directed to a method of treating and inhibiting tumor growth by the administration of tumor cells transfected with DNA encoding the B7 protein present in B-lymphocytes. This transfection stimulates the immune system to mount a response against the tumor cells, both B7-transfected and non-transfected.

Figure 4:
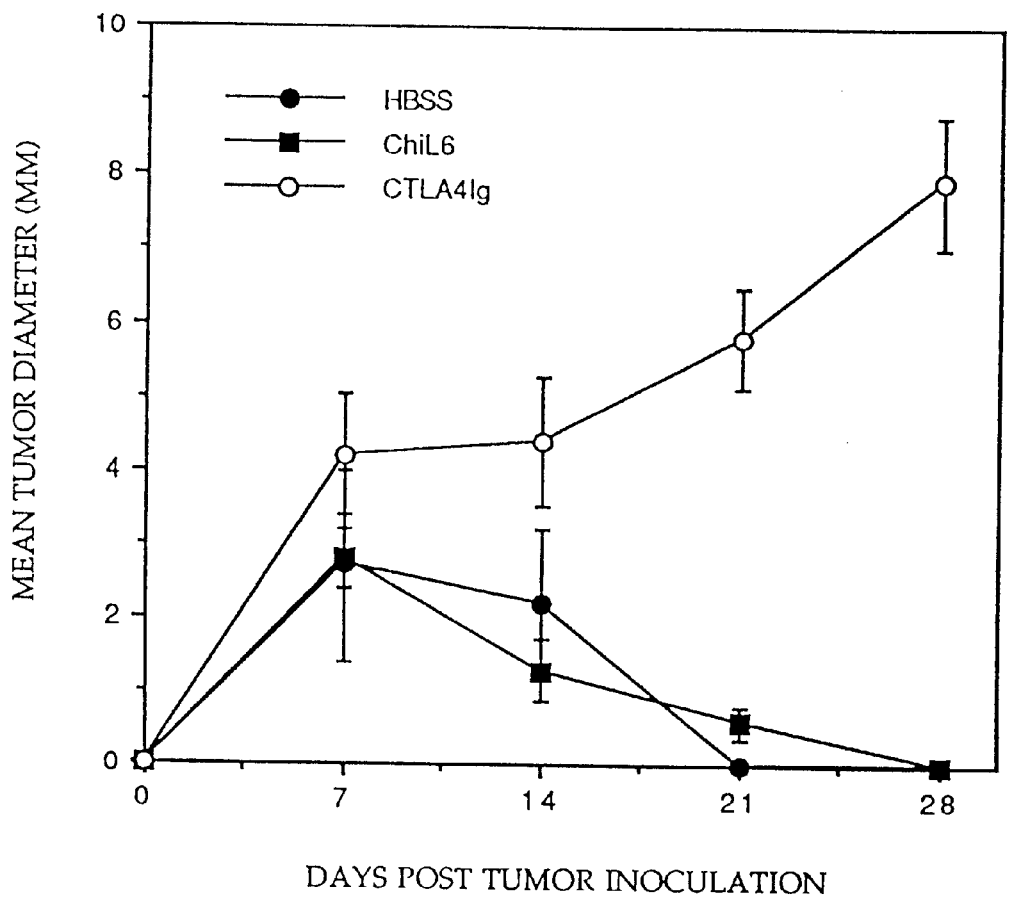
FIG. 4 illustrates that CTLA4Ig blocks rejection of B7+ E7C3 cells. C3H/HeN mice were injected subcutaneously on the back with 5×10⁶ BC22 cells which had been premixed with 50 μg CTLA4Ig. CTLA4Ig treatment was continued for a total of two weeks by intravenous injection every other day (50 μg per treatment). Mice treated with either Hank's balanced salt solution (HBSS) or chimeric mAb L6 (ChiL6) were used as controls. Tumor growth was monitored as described in FIG. 2. This experiment was repeated with similar results.

We have demonstrated that transfection of the T cell costimulatory molecule B7 into murine tumor cells expressing the HPV-16 E7 open reading frame caused them to be rejected when transplanted into immunocompetent, syngeneic hosts. Rejection required both E7 and B7 expression, and was T cell mediated, since B7⁺ and B7⁻ tumors grew equally well in nude mice. The immune response causing rejection was B7-dependent, since treatment of mice with CTLA4Ig, a soluble high avidity receptor for B7, blocked rejection of B7⁺E7⁺ tumor cells (FIG. 4). Rejection of B7⁺ tumors led also to rejection of B7⁻E7⁺ tumor cells at distant sites.

There is much evidence that B7 can costimulate T cell activation in vitro (Linsley et al. (1991) J. Exp. Med. 174:561–569; Gimmi et al. (1991) Proc. Natl. Acad. Sci. USA 88:6575–6579; Kuolova et al. (1991) J. Exp. Med. 173:759–762; Damle et al. (1992) J. Immunol. 148:1985–1992). In the present invention these observations are extended by directly demonstrating a role for B7 in stimulating T cell activation in vivo, as well as for regulating tumor immunity. This data, therefore, support a "two signal" model for lymphocyte activation. According to this model, the transfected E7 tumor antigen, as presented via MHC class I molecules, provides an antigen-specific "signal one" which triggers the TCR complex on reactive T cells. B7 expressed on tumor cells provides an antigen non-specific "signal two" by binding to its receptors CD28 and CTLA-4 on T cells, thereby costimulating the immune response to E7⁺ tumors.

It is well established that anti-CD28 mAbs can stimulate the production of several lymphokines during T cell activation (June et al. (1990) Immunol. Today 11:211–216), and it has been shown more recently that engagement of CD28 by its counter-receptor, B7, stimulates T cell production of IL-2 (Linsley et al. (1991) J. Exp. Med. 174:561–569; Gimmi et al. (1991) Proc. Natl. Acad. Sci. USA 88:6575–6579). Taken together, these studies suggest that CD28 functions as a major regulator of T cell lymphokine production. It is not currently known whether CTLA-4 has a similar function. Results from experiments involving transfection of lymphokine genes into tumors (Tepper et al. (1989) Cell 57:503–512; Fearon et al. (1990) Cell 60:397–403; Gansbacher et al. (1990) Cancer Res. 50:7820–7825; Gansbacher et al. (1990) J. Exp. Med. 172:1217–1224; Ley et al. (1991) Eur. J. Immunol. 21:851–854; Golumbek et al. (1991) Science 254:713–716) have suggested that tumor-reactive lymphocytes are sometimes present in tumor-bearing animals, but are unable to cause rejection because of insufficient availability of T cell lymphokines. The present study suggests that lack of CD28 receptor triggering may be a contributing factor to deficient T cell lymphokine production in tumor-bearing animals.

Figure 5:
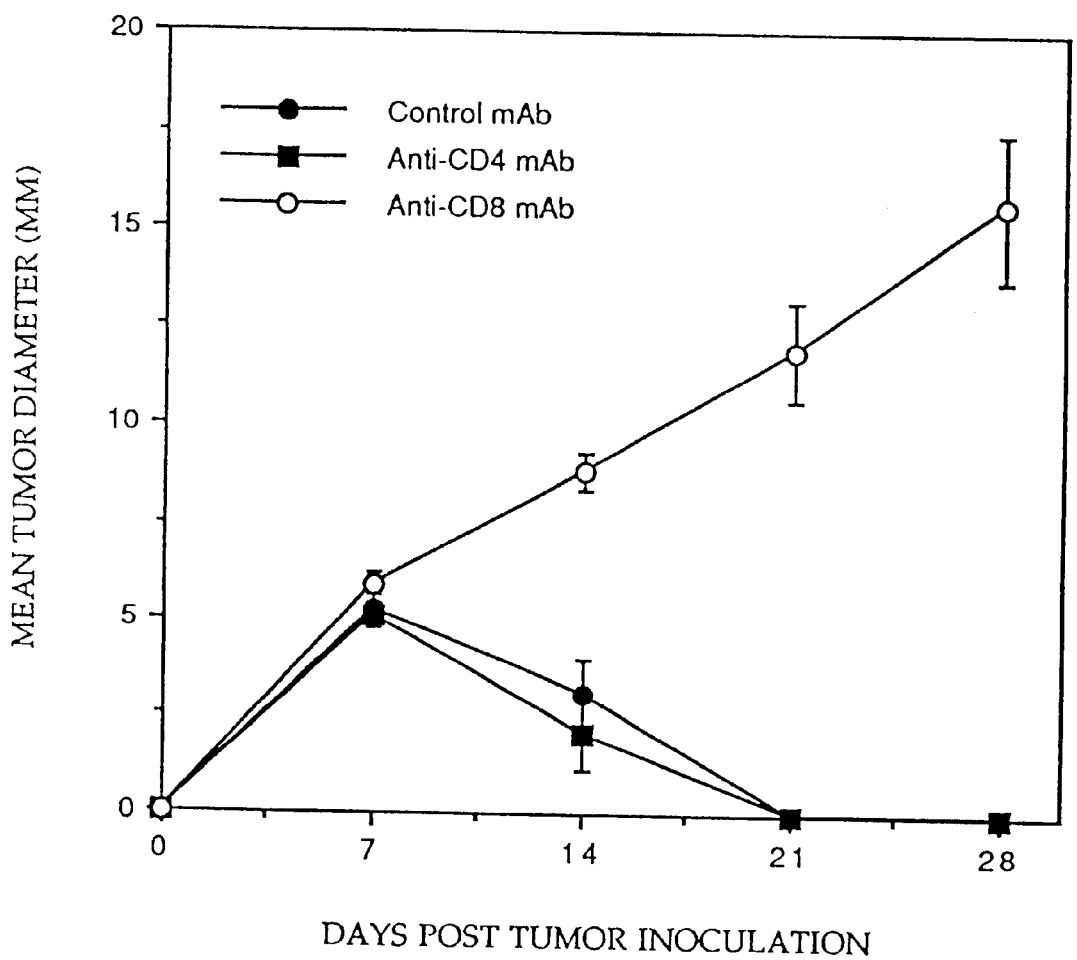
FIG. 5 illustrates the rejection of B7+ E7C3 tumors is mediated by CD8+ T cells. C3H/HeN mice were injected intraveneously twice at weekly intervals with purified anti-CD4 or anti-CD8 antibodies at 1 mg/mouse. The same amount of the anti-human CD5 antibody 10.2 was injected as a control. Mice were then inoculated subcutaneously with BC16 cells and tumor growth was assessed as described in FIG. 2. Similar results were obtained in another experiment.

Antitumor immunity was abrogated in vivo and in vitro by anti-CD8, but not anti-CD4 mAbs, and CD8⁺ CTL were readily generated from mice which had rejected B7⁺E7⁺ tumors. CD8⁺ CTL are also responsible for rejection of B7⁻E7⁺ (Chen et al. (1991) Proc. Natl. Acad. Sci. USA 88:110–114; Chen et al. (1992) J. Immunol. 148:2617–2621) tumors in immunization and challenge experiments. Tumor rejection in vivo and cytolysis in vitro did not require expression of B7 on target cells (FIGS. 6 and 7), indicating that effects of B7 on the cytolytic effector phase (Azuma et al., (1992) J. Exp. Med. 175:353–360) could not explain the results. Rather, the role of B7 in these experiments was most likely to directly trigger lymphokine production and expansion of CD8⁺ CTL. CD4⁺ Th cells did not appear to play a major role in generation of these CTL, since in vivo depletion of >95% of CD4⁺ T cells did not block tumor rejection (FIG. 5). Recent studies have shown that B7 stimulates lymphokine production and clonal expansion of CD8⁺ T cells that express a transgenic TCR specific for anti-male (H-Y) antigen in the absence of CD4⁺ T cells, and there is also evidence that triggering of CD28 using specific mAbs induces CTL activity (Jung et al. (1987) Proc. Natl. Acad. Sci. 84:4611; Nijuis et al. (1990) Cancer Immunol. Immunother. 32:245–250. Stimulation of lymphokine release by CD28 triggering may have contributed to tumor rejection also by upregulating the expression of MHC class I molecules on tumor cells in vivo, or by recruiting inflammatory cells (FIG. 3) which assist in tumor destruction.

Blocking interactions between CD28/CTLA-4 and B7 in. vivo can lead to long term donor-specific graft survival (Lenschow et al. (1992) Science, 257:789–792), indicating that blocking costimulation of the CD28 receptor in the continued presence of foreign antigens leads to T cell unresponsiveness. Since circulating tumor antigens and immune complexes contribute to the escape of tumors from immunological rejection (Hellström and Hellström (1991) Principles of Tumor Immunity: Tumor Antigens, In: The Biologic Therapy of Cancer. DeVita, Jr. et al., Eds., J. B. Lippincott Co., Philadelphia, pp. 35–52), it is tempting to speculate that continued TCR stimulation by foreign antigens presented on or released from tumors in the absence of adequate costimulation by molecules such as B7 will suppress antitumor immunity.

The failure of many tumors to induce a rejection response in immunization and challenge experiments has been interpreted as evidence that these tumors fail to express foreign antigenic determinants (Hewitt et al. (1976) Br. J. Cancer 33:241–259). Tumors may fail to induce an immune response not because they lack foreign antigenic determinants, but because they fail to deliver or elicit T cell costimulatory signals. Such tumors may fail to express adequate T costimulatory molecules to directly stimulate expansion of CD8⁺ T cells which recognize internally processed tumor antigens. Alternatively, B7⁺ APC may fail to present adequate amounts of antigenic peptides to elicit a CD4+ T cell response. In other words, tumors may be nonimmunogenic because "signal one" or "signal two" is lacking.

Nonimmunogenic K1735-M2 cells were not rejected even after transfection with B7, so the approach used here does not overcome the lack of immunogenicity of some tumors. However, other molecules besides B7 may be also needed to obtain optimal T cell costimulation in vitro (van Seventer et al. (1991) Curr. Opinion Immunol. 3:294–303). Whether molecules such as ICAM-1, LFA-3, VCAM-1 (van Seventer et al. (1991) Curr. Opinion Immunol. 3:294–303) or the heat stable antigen (Liu, Y. et al. (1992) Eur. J. Immunol., 22:2855–2859) are capable of stimulating antitumor immunity is not currently known. The experimental approach presented here suggest the possibility that rejection of "nonimmunogenic" tumors, such as K1735-M2, may be induced by transfecting them with costimulatory molecules other than, or in addition to B7.

Finally, these data suggest that antitumor immune responses in cancer patients might be increased by stimulating the CD28 receptor in vivo. It may be possible to upregulate B7 (or target B7 to the tumor cell surface) expression on tumors in vivo, or on APC presenting potentially antigenic peptides from tumor cells. It may also be possible to transfer B7 into tumor cells in vitro, and to expand populations of tumor-reactive lymphocytes for in vivo infusion by exposure of patient lymphocytes to their B7+ tumor cells. A long range goal would be to generate systemic immunity to a tumor antigen by introducing B7 directly into tumor cells in vivo. Since B7+E7+ tumor cells stimulated immunity to B7−E7+ tumors at distant sites (FIG. 7), generation of a therapeutically beneficial rejection response may only require introduction of B7 into some tumor cells in vivo.

Having generally described this invention, a further understanding can be obtained by reference to certain specific examples which are provided herein for purposes of illustration only and are not intended to be limiting unless otherwise specified.

For the pupose of carrying out the studies illustrated in the Examples described herein, the following experimental procedures and protocols were utilized.

EXPERIMENTAL PROCEDURES

Mice

Female C3H/HeN mice, 6–8 weeks old, were bought from Charles River Breeding Laboratories (Wilmington, Mass.). Female BALB/c (nu/nu) mice, 4–8 weeks old, were bought from Harlan Sprague Dawley Co. (Indianapolis, Ind.).

Cell Lines

K1735-M2 cells were of C3H/Hen (H-$2^k$) mouse origin (Fidler and Hart, 1981). E7C3 and E6B2 are K1735-M2 transfectants expressing HPV-16 E7 or E6 gene respectively (Chen, et al. (1992) J. Immunol. 148:2617–2621). Lines p2555 and 16N7 are derived from a fibrosarcoma NCTC2555 (H-$2^k$) (American Type Culture Collection, Rockville, Md.) and transfused with parental pLXSN retrovirus or retroviruses containing HPV-16 E7 gene, respectively (Chen et al. (1992) J. Immunol. 148:2617–2621). The p815E7 is a DBA/2-derived mastocytoma (H-$2^d$) (ATCC) transduced with retroviral HPV-16 E7 (Halbert et al. (1991) J. Virol. 65:4417). All cells were maintained at 37° C. in Dulbecco's modified Eagle's medium (DMEM) containing 10% fetal calf serum (Sterile System, HyClone, Logan, Utah).

Cloning and Transfection of Murine B7

A DNA fragment encoding murine B7 (Freeman et al. (1991) J. Immunol. 143:2714–2722) was amplified by PCR as described (Liu et al. (1992) Eur. J. Immunol. In Press) and cloned into a pLN expression plasmid vector (kindly provided by A. Aruffo of the Bristol-Myers Squibb Pharmaceutical Research Institute, Seattle, Wash.). The resulting expression construct (pmurB7) was cotransfected into E7C3 cells with an expressible mutant containing dihydrofolate reductase (DHFR) cDNA ($D^R$/pic, a gift of S. Yarnold and P. Fell, Bristol-Myers Squibb Pharmaceutical Research Institute, Seattle, Wash.) using lipofections reagent (Gibco BRL, Grand Island, N.Y.). Transfectants were selected in DMEM plus 10% fetal bovine serum (FBS) containing 0.33 $\mu$M MTX. Individual MTX-resistant colonies were picked and analyzed for B7 expression by CTLA-4Ig binding (Linsley et al. (1991) J. Exp. Med. 174:561–569). Pooled colonies (~25) were also separated into B7 positive (PB7+) and B7 negative (PB7−) population by two rounds of sorting by flow cytometry. K1735-M2 cells were also cotransfected by pmurB7 and PCMIpola (Stratagene, La Jolla, Calif.) and selected in DMEM with 10% FBS containing 1 mg/ml G418 (Gibco, Grand Island, N.Y.).

Antibodies

Hybridomas were purchased from ATCC, which produced rat anti-mouse CD4 (L3T4) mAb GK1.5, rat anti-mouse CD8 (Lyt2.1) mAb 116-13.1, and murine anti-H-$2K^kD^k$ mAb 15-3-1S. The rat anti-human CD5 mAb 10.2 was used as control (Chen et al. (1991) Proc. Natl. Acad. Sci. USA 88:110–114). Hybridomas were injected intraperitoneally into pristane-treated nude mice and ascites was purified by affinity chromatography on protein A coupled to Sepharose CL-4B (Pharmacia Fine Chemicals, Piscataway, N.J.). Rabbit anti-asialoGM1 sera were purchased from Wako Chemicals USA. Inc. (Richmond, Va.) CTLA-4Ig, a soluble fusion protein between the extracellular domain of human CTLA-4 and a human Ig C$\gamma$ chain, was described (Linsley et al. (1991) J. Exp. Med. 174:561–569). Purified human-mouse chimeric mAb L6 (having human C$\gamma$1 Fc portion) Ig was prepared as described (Liu et al. (1987) Proc. Natl. Acad. Sci. USA 84:3439–3443).

Immunostaining and Flow Cytometry Analysis

The methods for immunostaining of B7 expression have been described (Linsley et al. (1991) J. Exp. Med. 174:561–569). Briefly, transfected cells were first incubated with either chimeric L6 or CTLA-4Ig at 10 $\mu$g/ml in DMEM containing 10% FBS for 30 minutes at 4° C. Cells were then washed and incubated for an additional 1 h at 4° C. with fluorescein isothiocyanate (FITC)-conjugated goat-anti-human Ig C$\gamma$ serum (Tago Corp., Burlingame, Calif.). For analysis of CD4 and CD8 expression on spleen cells, single cell suspensions were incubated with anti-CD4 (GF1.5) or anti-CD8 (53.6) mAb conjugated with FITC at 4° C. for 30 min and washed twice with medium. A total of 10,000 cells was then analyzed by flow cytometry (Becton Dickinson & Co., Mountain View, Calif.).

In Vivo Tumor Rejection

Mice, in groups of five or ten, were each given a subcutaneous injection on the shaved flank at 5×10$^6$ cells. Tumor size was assessed by measuring two perpendicular diameters in millimeters (mm) by a caliper weekly for each animal. The results were expressed as mean diameters of tumors.

In Vivo Depletion of T Cells

For in vivo depletion experiments, mice were injected intravenously twice with purified mAbs to CD4 (GK1.5) or CD8 (116-13.1) in dosages of 1 mg/mice 7 days before and on the day of tumor inoculation. The same amount of anti-human CD5 mAb 10.2 was used as control. Four to five weeks later, mice were killed and spleen cell suspensions were prepared and examined with flow cytometry by FITC-labeled anti-CD4 and CD8 antibodies for efficiency of depletion. Larger than 95% of depletion of specific T cell subset was consistently achieved without affecting other subsets.

Histologic Evaluation

Tissues were removed from the site of tumor cell inoculation 10 days after injection, fixed in 10% formalin, blocked in paraffin, sectioned at 4–6 $\mu$m and was stained with hematoxylin and eosin (H & E). Microscopic evaluation was performed as indicated in FIG. 4.

CTL Assays

Experimental procedures to measure CTL activity were described (Chen et al. (1992) J. Immunol. 148:2617–2612). In brief, the spleens from mice were removed 4–10 weeks after tumor inoculation and the spleen cells ($6 \times 10^6$) were cocultivated with $\gamma$-irradiated (10,000 rad) 16N7 cells ($1 \times 10^5$) in 2 ml medium per well in a 24-well plate (Costar, Cambridge, Mass.). Six days later cells were harvested and counted as effector cells. Two million target cells were labeled with 250 $\mu$Ci of $^{51}$Cr (New England Nuclear, Boston, Mass.) for 45 min (for p815E7) or overnight (for p2555 and 16N7 cells), after which labeled target cells (5,000 cells/well) were cocultivated with effector cells at different effector/target (E: %) ratio for 4 hr. Supernatants were collected and counted with a $\gamma$-counter. Percent specific lysis was calculated as follows: 100×{(experimental cpm-spontaneous cpm)/(maximal cpm - spontaneous cpm)}. Spontaneous release in the absence of CTL was between 5%–20% of the maximal release by Triton X-100 (1:100) in all experiments. In cell depletion assays, effector cells at $1 \times 10^6$/ml were pretreated for 60 min at 37° C. with 30 $\mu$g/ml of mAbs as indicated in the presence of $\frac{1}{10}$ diluted rabbit complement (Cedarlane Laboratories, Homby, Ontario, Canada) and washed three times before use.

EXAMPLE 1

Figure 1:
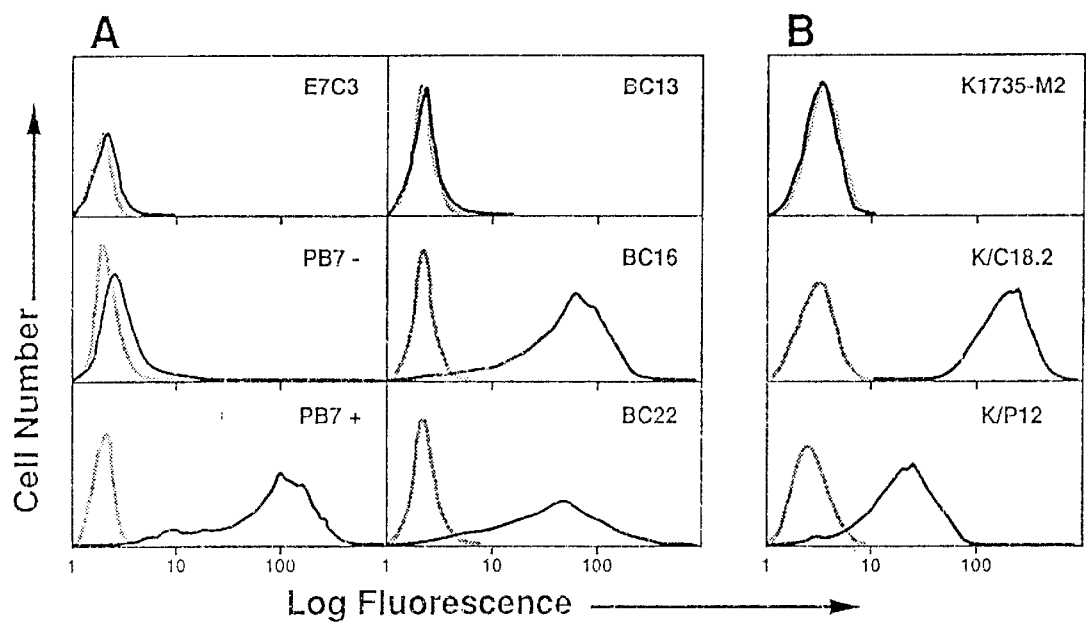
FIGS. 1A and 1B illustrate the expression of B7 on transfected cell lines. Cells were stained with either CTLA4Ig (solid lines) or the control mAb chimeric L6 (dotted lines) followed by FITC-conjugated goat-anti-human Ig Cγ serum as described in Experimental Procedures. A total of 5,000 cells was analyzed for each sample. Panel A shows E7C3 cells and its B7 transfectants, and panel B shows K1735-M2 cells and its B7 transfectants.

Transfection And Expression Of Murine B7 In E7C3 And K1735-M2 Tumor Cell Lines The murine melanoma cell line E7C3 (B7$^-$E7$^+$) was derived by transfecting the E7 gene of HPV-16 (Chen et al. (1991) Proc. Natl. Acad. Sci. USA 88:110–114) into the K1735-M2 line (Fidler and Hart, 1981). E7C3 cells were co-transfected with pmB7 and D$^R$/pic as described in Experimental Procedures and transfectants were selected for methotrexate (MTX) resistance. K1735-M2 cells were co-transfected with pmB7 and pCM1neoPolyA and selected for neomycin resistance. Drug-resistant cell clones were tested for expression of B7 by flow cytometry after indirect immunofluorescent staining with CTLA4Ig, a soluble form of the extracellular domain of CTLA-4 which binds human (Linsley et al. (1991) J. Exp. Med. 173:721–730) and murine (Liu et al. (1992) Eur. J. Immunol., 22:2855–2859) B7 with high avidity. Three E7C3 transfectants were selected for further study; two of these (BC16 and BC22) stained positive for B7 and one (BC13) stained negative. A pool of ~25 M-resistant clones from the E7C3 transfection were also sorted by flow cytometry into B7 positive (PB7$^+$) and B7 negative (PB7$^-$) populations. From the K1735-M2 transfection, two B7-positive clones (K/18.2 and K/P12) were selected. Levels of B7 expression on these cells were compared by flow cytometry (FIG. 1). In other experiments, all selected cell lines showed roughly similar levels of HPV-16 E7 gene expression by semiquantitative reverse transcriptase-coupled polymerase chain reaction (PCR) assay. All lines expressed low levels of MHC class I molecules as judged by flow cytometry, and also showed similar induction of MHC class I molecules following treatment with $\gamma$ interferon.

EXAMPLE 2

B7$^+$E7C3 Tumors Regress In Vivo

To examine whether B7 expression enhances T cell immunity against E7C3 tumors, B7$^+$ and B7$^-$ transfectants were injected subcutaneously into C3H/HeN mice and T cell-deficient nude mice (BALB/c nu/nu) to test their tumorigenicity (Table 1). E7C3 cells were less tumorigenic in naive C3H/HeN mice than parental K1735-M2 cells, but both lines showed similar tumorigenicity in nude mice (Table 1). These results suggest that a T cell-mediated immune response was induced by the E7C3 tumor in immunocompetent mice which slowed tumor growth but did not lead to tumor eradication in most mice, since only $\frac{2}{15}$ mice (~13%) rejected their tumors.

In contrast, inoculation of BC16, BC22, or PB7$^+$ cells into C3H/HeN mice led to transient tumor growth followed by regression in 100% of the animals within 2–3 weeks (Table 1). Clone BC13 and the PB7$^-$ population formed tumors which grew similar to parental E7C3 cells (10% and 0% regression respectively). A photograph of E7C3 and PB7$^+$ injected C3H/HeN mice is shown in FIG. 2A, and the kinetics of tumor growth of E7C3 and several transfected derivatives are shown in FIG. 2B. All E7C3-derived cells formed tumors in nude mice (Table 1). While expression of B7 in E7C3 cells led to tumor rejection by C3H/HeN mice, expression of B7 by two K1735-M2 derived, E7-negative clones (K/18.2 and K/P12) did not.

Figure 3:
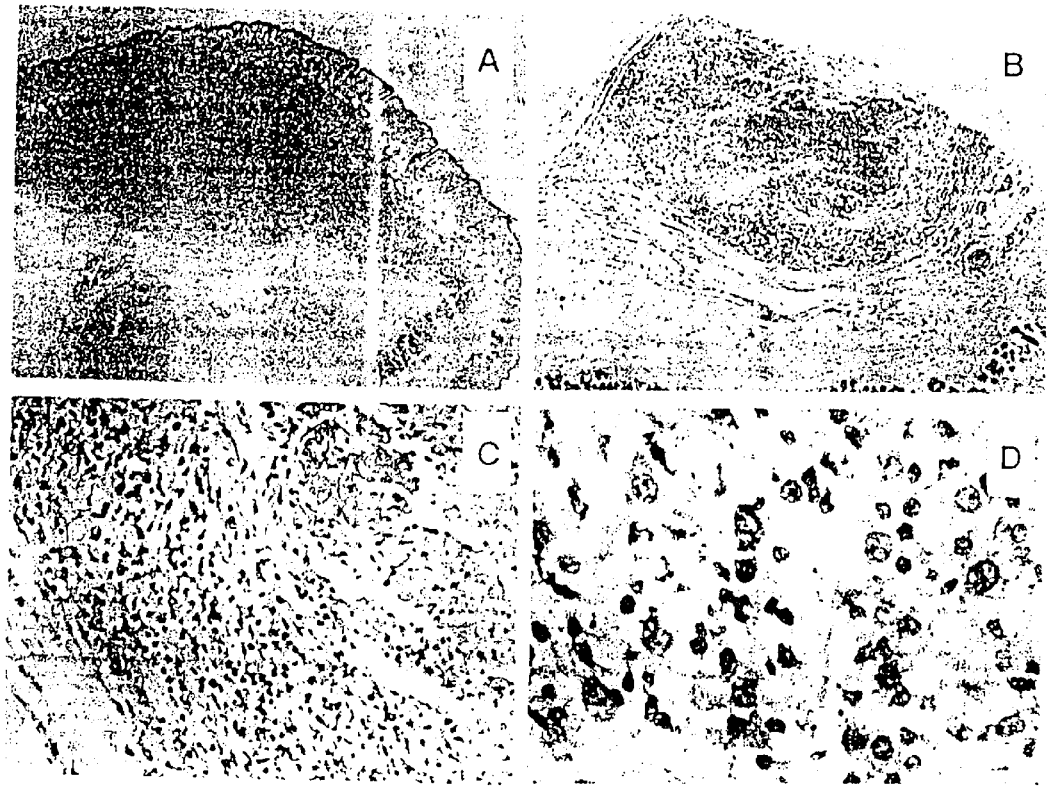
FIG. 3 panels A, B, C and D illustrate the histology of tumors induced by B7− or B7+ E7C3 cells. C3H/HeN mice were injected subcutaneously with PB7− cells (panel A) or PB7+ cells (panels B–D). Ten days after injection, tumors were excised and prepared for histological analysis. (A) Tumor induced by PB7− cells. Note the presence of unencapsulated tumor nodules extending into superficial dermis. Focal necrosis of neoplastic cells can be seen (66× magnification). (B) Tumor induced by PB7+ cells. Note the presence of a large central area of tumor necrosis and infiltration of inflammatory cells among the tumor cells (66× magnification). (C) Higher magnification from (B). Note the prominent infiltration of inflammatory cells (660× magnification). (D) Larger magnification from (B). The tumor cells vary in size and shape and have pale eosinopbilic cytoplasm with indistinct cell borders. Lymphocytes and macrophages are seen (1350× magnification).

Histologic sections from growing B7$^-$ tumors and B7$^+$ tumors undergoing rejection are shown in FIG. 3. A tumor induced by PB7$^-$ cells 10 days after injection showed progressively growing neoplastic cells extending from the deep dermis into the superficial dermis. Histologic sections from E7C3-induced tumors appeared similar. Examination of a PB7$^+$ cell tumor revealed a severely necrotic core, as shown in FIG. 3B, surrounded by a thin rim of neoplastic cells infiltrated with inflammatory cells (FIG. 3B–D). Similar results were obtained with BC16 tumors.

TABLE 1

Summary Of Tumorigenic Characteristics Of B7$^+$ E7C3 Cell Lines In Immunocompetent And Nude Mice

| | | | Tumor Status 21 Days After Subcutaneous Inoculation Into Mice | | | |
|---|---|---|---|---|---|---|
| | | | C3H/HEN | | BALB/c (nu/nu) | |
| Cell Lines | E7 | B7 | Tumor Incidence (%)[1] | Range of Mean Tumor Diameter (mm)[2] | Tumor Incidence (%) | Range of Mean Tumor Diameter (mm) |
| E7C3 | + | – | 13/15 (87) | 0–12 | 15/15 (100) | 14–19 |
| PB7 | + | – | 9/10 (90) | 0–7 | 10/10 (100) | 15–20 |
| BC13 | + | – | 10/10 (100) | 4–8 | 10/10 (100) | 18–24 |

TABLE 1-continued

Summary Of Tumorigenic Characteristics Of
B7+ E7C3 Cell Lines In Immunocompetent And Nude Mice

| | | | Tumor Status 21 Days After Subcutaneous Inoculation Into Mice | | | |
|---|---|---|---|---|---|---|
| | | | C3H/HEN | | BALB/c (nu/nu) | |
| Cell Lines | E7 | B7 | Tumor Incidence (%)[1] | Range of Mean Tumor Diameter (mm)[2] | Tumor Incidence (%) | Range of Mean Tumor Diameter (mm) |
| PB7+ | + | + | 0/10 (0) | 0 | 10/10 (100) | 14–21 |
| BC16 | + | + | 0/9/ (0) | 0 | 10/10 (100) | 16–21 |
| BC22 | + | + | 0/15 (0) | 0 | 10/10 (100) | 5–10 |
| K1735-M2 | – | – | 10/10 (100) | 15–23 | 15/15 (100) | 16–26 |
| K/18.2 | – | + | 10/10 (100) | 12–24 | ND[3] | ND[3] |
| K/P12 | – | + | 9/9 (100) | 13–21 | ND[3] | ND[3] |

[1]Aliquots of 5 × 106 cells in 0.1 ml HBSS were injected subcutaneously into 6–8 week-old C3H/HeN or BALB/c (nu/nu) mice. Tumor size was assessed by measuring two perpendicular diameters in mm by a caliper weekly for each animal. Mice with tumors <2 mm in diameter were scored negative on tumor incidence.
[2]The results were expressed as mean diameters of tumors. The range of mean tumor diameters in the indicated number of mice is shown.
[3]Not Done.

EXAMPLE 3

Rejection Of B7+ E7C3 Cells Is Mediated By A B7-Dependent Immune Response

To determine whether rejection of B7+E7+ tumor cells is caused by a B7-mediated immune response, we tested whether tumor rejection was blocked by in vivo treatment with CTLA4Ig, which blocks B7 binding to both CD28 and CTLA-4 and thereby suppresses immune responses in vitro and in vivo (Linsley et al. (1991) J. Exp. Med. 173:721–730, Linsley et al. (1992) Science 257:792–795; Lenschow et al. (1992) Science 257:792–795). BC22 cells were admixed with 50 μg CTLA4Ig prior to injection into C3H/HeN mice, followed by injection of 50 μg CTLA4Ig intraveneously every other day for 12 days; this regime of CTLA4Ig treatment was previously used to block rejection of pancreatic islet cell xenografts in mice (Lenschow et al. (1992) Science 257:792–795). As a control, equivalent amounts of an isotype-matched chimeric monoclonal antibody (mAb) L6 (Fell et al. (1992) J. Biol. Chem. 267: 15552–15558 were used. As shown in FIG. 4, CTLA4Ig treatment prevented rejection of tumors caused by BC22 cells, whereas the control mAb did not. Similar results were obtained with BC16 cells. These results indicate that the rejection of B7+ E7C3 cells in immunocompetent syngeneic host is mediated by interactions between B7 and its receptors.

EXAMPLE 4

B7 Expression Induces A CD8+ T Cell Response To E7+ Tumors

To analyze the roles of T cell subsets in the rejection of B7+ E7C3 tumor cells, mice were injected with mAbs to either CD4+ or CD8+ T cells to specifically deplete these cells in vivo. This procedure removed >95% of either population of T cells without effect on other cell populations, as judged by flow cytometry. The removal of CD8+ T cells completely abrogated the rejection of B7+ E7C3 cells, including both BC16 (FIG. 5) and BC22. On the contrary, injection of anti-CD4 mAb, or the control mAb, did not affect tumor rejection (FIG. 5). These results indicate that the rejection induced against B7+ E7C3 cells was primarily mediated by CD8+ T cells.

Figure 6:
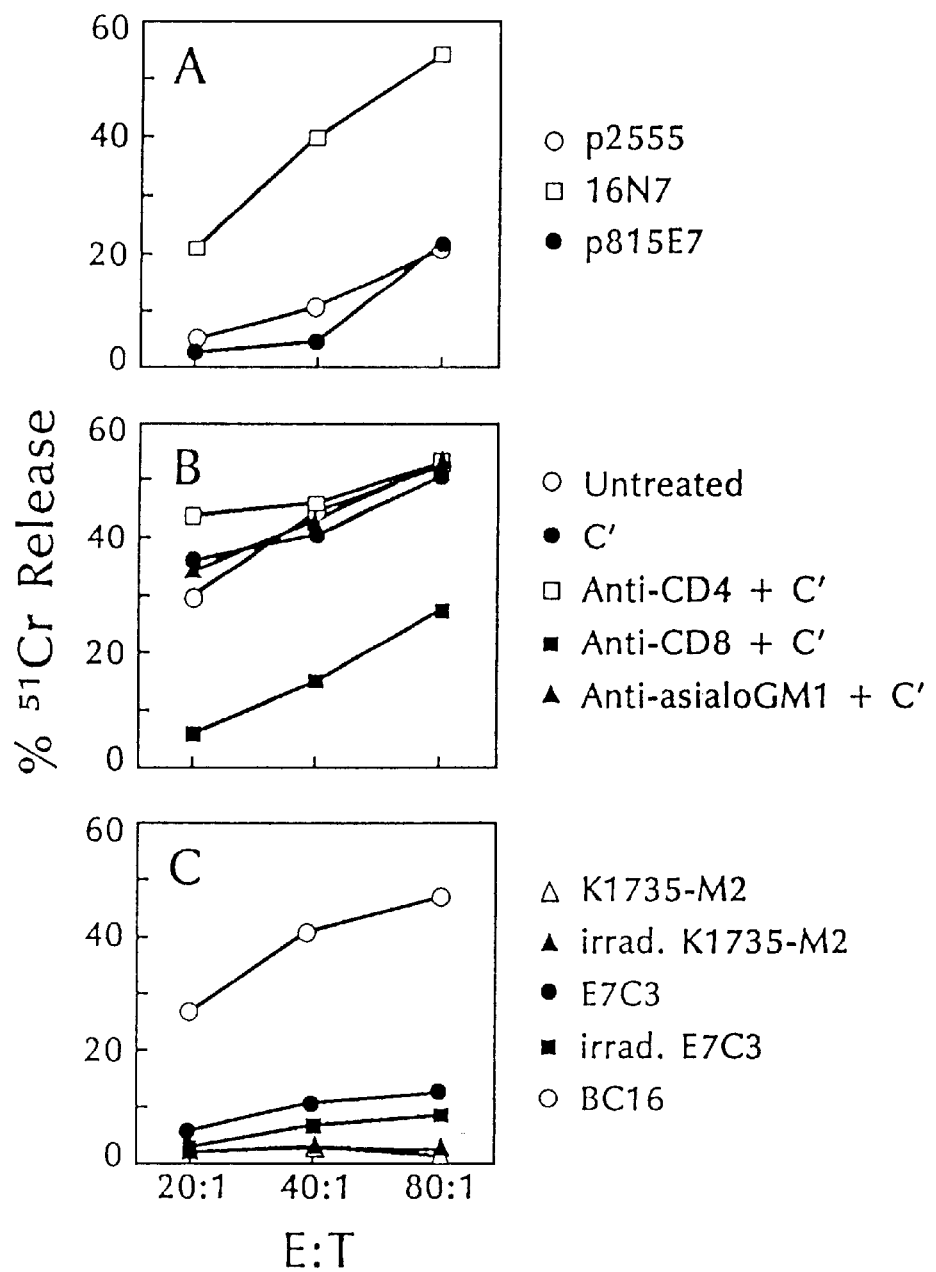
FIG. 6 panels A, B and C illustrate that CTL are generated from mice inoculated with B7+ E7C3 cells.

Injection of B7+E7+ tumor cells led to CTL generation (FIG. 6). Tumor cells were injected subcutaneously into mice, spleens were removed and spleen cells were subjected to secondary stimulation with E7+ tumor cells in vitro to generate polyclonal CTL (Chen et al. (1992) J. Immunol. 148:2617–2621). Cytotoxicity was measured against $^{51}$Cr-labeled 16N7 target cells; these are MHC class I (H-2$^k$) positive, E7 positive fibrosarcoma cells (Chen et al. (1992) J. Immunol. 148:2617–2621) which gave more consistent results in in vitro cytotoxicity assays than E7C3 cells. Strong CTL activity was detected with splenocytes taken from animals injected with BC16 cells after restimulation in vitro by 16N7 cells (FIG. 6A). The CTL did not lyse control fibrosarcoma cells which did not express E7 (p2555 cells) or E7-expressing cells (p815E7) of different MHC haplotype (FIG. 6A), suggesting that target cell lysis was antigen-specific and MHC class I-restricted. Cytolytic activity was greatly decreased by pretreatment of the effector cells with an anti-CD8 mAb in the presence of complement, but not by treatment with anti-CD4 or anti-NK cell antibodies (FIG. 6B). Levels of cytolytic activity were measured in spleen cells from mice injected with E7C3, BC16 or irradiated E7C3 cells and subjected to secondary in vitro stimulation with 16N7 cells (FIG. 6C). Only spleen cells from mice injected with BC16 cells had significant CTL activity. Taken together, these results indicate that the expression of B7 on E7C3 cells augments the induction of CD8+ CTL specific for E7+ tumor cells irrespective of the expression of B7.

EXAMPLE 5

Induction By B7+ E7C3 Cells Of Antitumor Immunity Against B7− E7C3 Tumors At A Distant Site To determine whether T cell immunity induced by B7+ E7C3 cells was effective towards B7−E7C3 cells transplanted at a distant site, C3H/HeN mice were injected with BC22 cells, E7C3 cells or medium alone on one flank and monitored the growth of simultaneously injected E7C3 tumor cells on the other flank. The growth of E7C3 tumors was significantly inhibited in animals having BC22 cells inoculated on the opposite flank; ⅘ of these mice completely rejected their tumors. Growth of E7C3 tumors was not affected in animals inoculated with medium or with B7−E7C3 tumors (FIG. 7A). Irradiated E7C3 tumors did not affect growth of E7C3 tumors inoculated on the opposite flank (data not shown). BC22 injection did not inhibit the growth of the E6B2 tumor, a K1735-M2-derived HPV-16 E6 transfectant (Chen et al. (1992) J. Immunol. 148:2617–2621) injected on the opposite flank (FIG. 7B). These results demonstrate that transplantation of B7+E7+ cells induced a systemic tumor rejection response against challenge with B7− parental E7C3 tumors, and that the rejection was specific for E7+ tumor cells.

Figure 8:
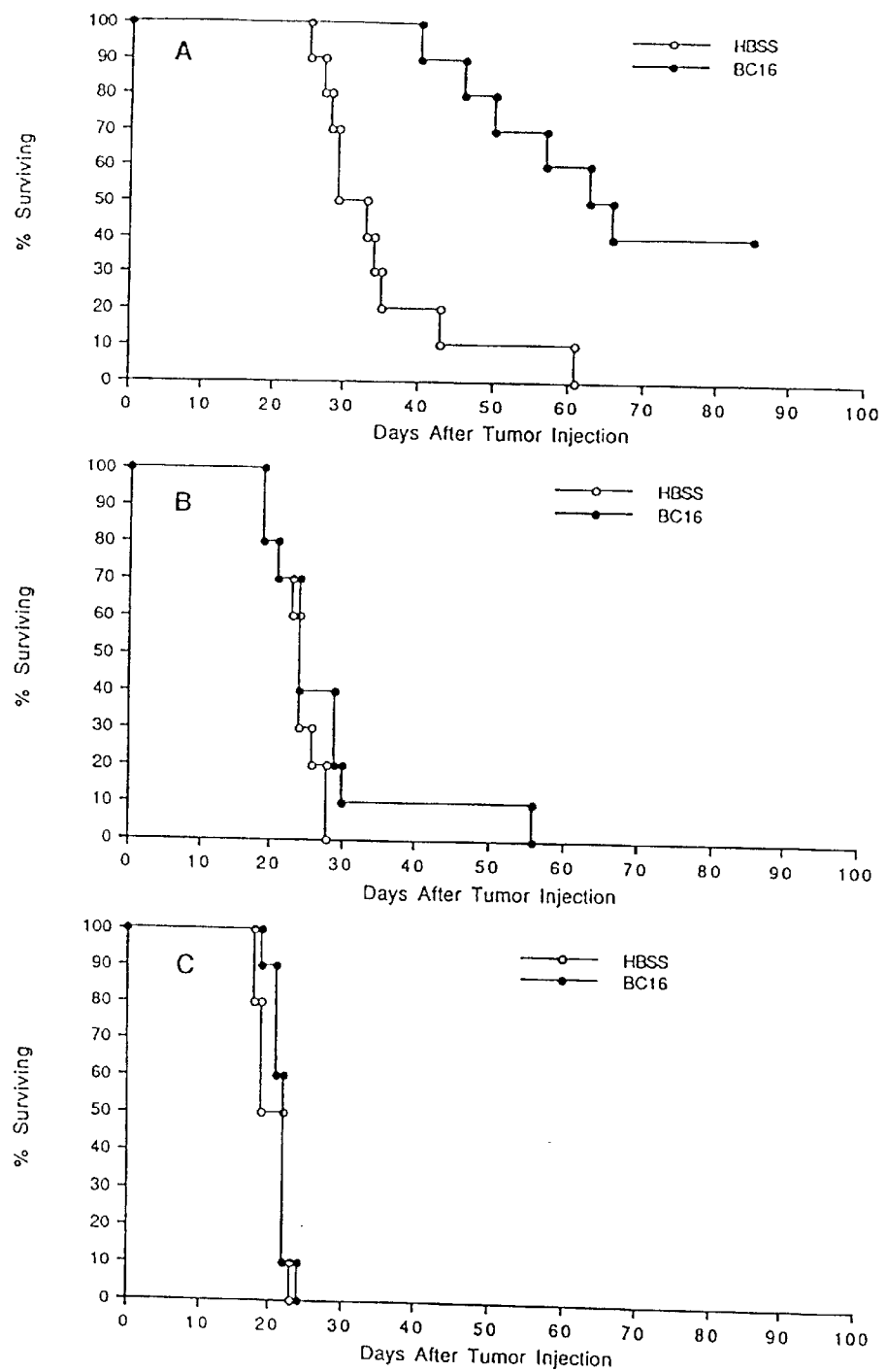

Further studies were then carried out using the BC16 cells for treatment of established metastatic tumors. C3H/HeN mice were separated into groups of 10 mice per group and each mouse injected intravenously with ×10$^5$ cells of either E7C3 cells (FIG. 8A), E6B2 cells (FIG. 8B) or K1735-M2 cells (FIG. 8C). Four days later, each mouse received an intravenous injection of 1×10$^6$ BC16 cells; this BC16 cell inoculation was repeated twice, at five day intervals. Survival of the animals was monitored and is illustrated in FIG. 8, which shows that BC16 cell administration significantly increased the survival of mice with E7C3 tumors and did not affect the survival of animals with other tumors.

EXAMPLE 7

Comparison of Tumor Induction by B7 Transfected and Non-Transfected Cells

Different tumor cell lines were each divided into two general groups. The first group of cells was not genetically altered (mock); while the second group of cells was transfected with DNA encoding B7 (B7$^+$ cells), such that the transfected tumor cells expressed B7.

Mice were then inoculated with a tumorigenic amount of cells (ranging from $1 \times 10^5$ to $5 \times 10^6$ cells per mouse) from either of the two groups for the different tumor cell lines, and tumor incidence was monitored at four weeks after inoculation. The results of these studies are shown in Table 2, and illustrate that tumor development from the B7 transfected cells was either eliminated or significantly inhibited compared to tumor incidence from the non-transfected tumor cell lines.

As demonstrated above, immunity generated by the E7 positive, B7 positive cells was effective in treating established tumors. Mice were injected intravenously with E7C3 cells capable of forming disseminated metastases to the lungs. Injection of E7 positive/B7 positive cells four days after establishment of E7C3 tumors prolonged survival of all treated mice and led to 40% long term survival.

In another study, K1735-M2 mouse melanoma cells, into which the gene for the p97 related tumor rejection antigen had been inserted (c162), were inoculated into immunocompetent mice and grew well, producing tumors. When these cells were transfected with B7 and the B7 positive c162 cells were inoculated into immunocompetent mice, no tumor development occurred.

Summary of Tumorigenic Characteristics of Cell Lines Expressing T Cell Costimulatory Molecule B7

| Tumor | Type | Strain | Immunogenicity* | Tumor incidence# Mock | Tumor incidence# B7 + cells |
|---|---|---|---|---|---|
| E7C3 (E7+) | melanoma | C3H/HeN | ++ | 18/20 | 0/30 |
| E6B2 (E6+) | melanoma | C3H/HeN | ++ | 20/20 | 0/10 |
| c162 (p97+) | melanoma | C3H/HeN | ++ | 19/20 | 0/10 |
| K1735-M2 | melanoma | C3H/HeN | − | 20/20 | 20/20** |
| EL-4 | lymphoma | C57BL/6 | + | 20/20 | 1/10 |
| B16 | melanoma | C57BL/6 | − | 15/15 | 2/10 |
| p815 | mastocytoma | DBA/2 | + | 15/15 | 0/5 |

*Judging from standard immunization and challenge experiments.
Tumor incidence at week 4 after tumor inoculation.
**Smaller tumors.

Similar results were obtained in studies with different tumor cell lines such as the EL-4 T cell mouse lymphoma, B16 melanoma and p815 mastocytoma.

The foregoing description and Examples are intended as illustrative of the present invention, but not as limiting. Numerous variations and modifications may be effected without departing from the true spirit and scope of the present invention.

We claim:

1. A method for generating a cytotoxic T lymphocyte response specific for cells of a tumor in a tumor-bearing patient, comprising removing a cell or cells from said tumor, transfecting said removed cell or cells with a nucleic acid molecule encoding the B7B cell surface protein, thereby creating transfected tumor cell or cells that express B7 on the cell surface, and administering to said tumor-bearing patient said transfected cell or cells.

2. The method of claim 1, wherein said cells of a tumor in a tumor-bearing patient are disseminated as metastases in said patient.

3. The method of claim 1, wherein said transfected tumor cell or cells express an extracellular portion of B7 which binds CD28/CTLA4.

4. The method of claim 1 wherein said tumor cells are human papillomavirus-infected cells.

5. The method of claim 1, wherein said transfected tumor cell or cells stimulate an immune response in said patient which results in rejection of both transfected and non-transfected tumor cells.

6. The method of claim 5 wherein metastases of said tumor are rejected.

7. A method for immunizing a patient against tumor cells comprising administering B7-transfected tumor cell membranes to said patient for a time period sufficient to produce an immune response which induces a rejection response to subsequent tumor cell exposure.

8. A cancer therapy comprising removing aliquots of tumor cells from a tumor-bearing patient, transfecting or transducing with a retroviral vector said tumor cells with DNA encoding the B7 B cell surface protein such that said tumor cells express B7, and readministering said B7-transfected cells to the patient wherein said B7-transfected cells are costimulatory for the production of an immune response directed to the rejection of said tumor cells in the patient.

9. A method of inhibiting growth of a tumor in a tumor-bearing mammal, comprising administering to said tumor-bearing mammal a therapeutically effective amount of B7-transfected cells of said tumor.

* * * * *